United States Patent
Waite

(10) Patent No.: US 9,626,866 B2
(45) Date of Patent: Apr. 18, 2017

(54) ACTIVE WARNING SYSTEM USING THE DETECTION OF DRIVER AWARENESS OF TRAFFIC SIGNS

(71) Applicant: Continental Automotive Systems, Inc., Auburn Hills, MI (US)

(72) Inventor: Sheldon G Waite, Lake Zurich, IL (US)

(73) Assignee: Continental Automotive Systems, Inc., Auburn Hills, MI (US)

( * ) Notice: Subject to any disclaimer, the term of this patent is extended or adjusted under 35 U.S.C. 154(b) by 0 days.

(21) Appl. No.: 14/457,430

(22) Filed: Aug. 12, 2014

(65) Prior Publication Data

US 2016/0049076 A1 Feb. 18, 2016

(51) Int. Cl.
| | | |
|---|---|---|
| *G08G 1/0967* | (2006.01) | |
| *G06K 9/00* | (2006.01) | |
| *B60K 28/00* | (2006.01) | |
| *G08G 1/0962* | (2006.01) | |
| *G08G 1/16* | (2006.01) | |
| *A61B 3/113* | (2006.01) | |

(Continued)

(52) U.S. Cl.
CPC ........ *G08G 1/096783* (2013.01); *A61B 3/113* (2013.01); *B60K 28/00* (2013.01); *G06K 9/00845* (2013.01); *G08G 1/09623* (2013.01); *G08G 1/096725* (2013.01); *G08G 1/165* (2013.01); *A61B 5/18* (2013.01); *A61B 5/746* (2013.01)

(58) Field of Classification Search
CPC ........... A61B 3/113; A61B 5/18; A61B 5/746; B60K 28/00; B60K 37/00; B60R 1/00; G08G 1/096783; G08G 1/09623; G08G 1/09626; G08G 1/16; G08G 1/165; G08G 1/0967; G08G 1/0968; G08G 1/096725; G06K 9/00791; G06K 9/00818; G06K 9/00825; G06K 9/00832; G06K 9/00845; G06K 9/00
USPC ....... 340/905, 435, 436, 438, 439, 457, 500, 340/501, 540, 573.1, 575, 576; 382/104, 382/181; 348/118, 120
See application file for complete search history.

(56) References Cited

U.S. PATENT DOCUMENTS

| | | |
|---|---|---|
| 6,560,529 B1 | 5/2003 | Janssen |
| 6,813,545 B2 | 11/2004 | Stromme |

(Continued)

FOREIGN PATENT DOCUMENTS

| | | |
|---|---|---|
| JP | 2005182307 A | 7/2005 |
| JP | 2012118804 A | 6/2012 |
| JP | 2012159469 A | 8/2012 |

OTHER PUBLICATIONS

Search Report dated Jan. 5, 2015, from corresponding GB Patent Application No. GB1415021.3.

*Primary Examiner* — Brian Wilson

(57) ABSTRACT

Traffic sign warnings are provided to a driver by optically scanning an area in front of the moving vehicle to obtain an image of said area in front of the moving vehicle. Road signs are recognized and their importance categorized. A driver's eyes are continuously scanned to determine whether the driver's eyes' ever focus on, or are directed to a detected and recognized road sign. Multiple different visual and/or audible warnings or alarms are generated based on the nature of a road sign, its proximity to the moving vehicle, and the driver's determined awareness of the road sign.

12 Claims, 7 Drawing Sheets

(51) Int. Cl.
*A61B 5/18* (2006.01)
*A61B 5/00* (2006.01)

(56) References Cited

U.S. PATENT DOCUMENTS

| | | |
|---|---|---|
| 8,223,038 B2 | 7/2012 | Bauer et al. |
| 8,233,670 B2 | 7/2012 | Moed et al. |
| 2005/0128063 A1* | 6/2005 | Isaji ..................... B60W 10/06 340/439 |
| 2006/0077050 A1* | 4/2006 | Takahashi .............. B60Q 9/008 340/435 |
| 2008/0042814 A1 | 2/2008 | Hurwitz et al. |
| 2011/0169625 A1 | 7/2011 | James et al. |
| 2014/0070934 A1* | 3/2014 | Chau ........................ B60R 1/00 340/438 |
| 2014/0118131 A1 | 5/2014 | Chiu et al. |
| 2014/0118169 A1 | 5/2014 | Hamberger et al. |

\* cited by examiner

ACTIVE WARNING SYSTEM USING THE DETECTION OF DRIVER AWARENESS OF TRAFFIC SIGNS

BACKGROUND

Road signs help keep traffic flowing smoothly and freely by helping drivers reach their destinations and let them know entry, exit and turn points in advance. Drivers who are warned in advance of a road entry, exit, turn, stop sign, traffic signal or speed limit by way of a road sign naturally tend to avoid mistakes that can cause collisions.

Virtually every vehicle driver will at some point inadvertently overlook a road sign. A method and apparatus for providing an active warning to a driver that a road sign has been missed or might have been missed would reduce collisions, improve traffic flow and safety.

DETAILED DESCRIPTION

Figure 1:
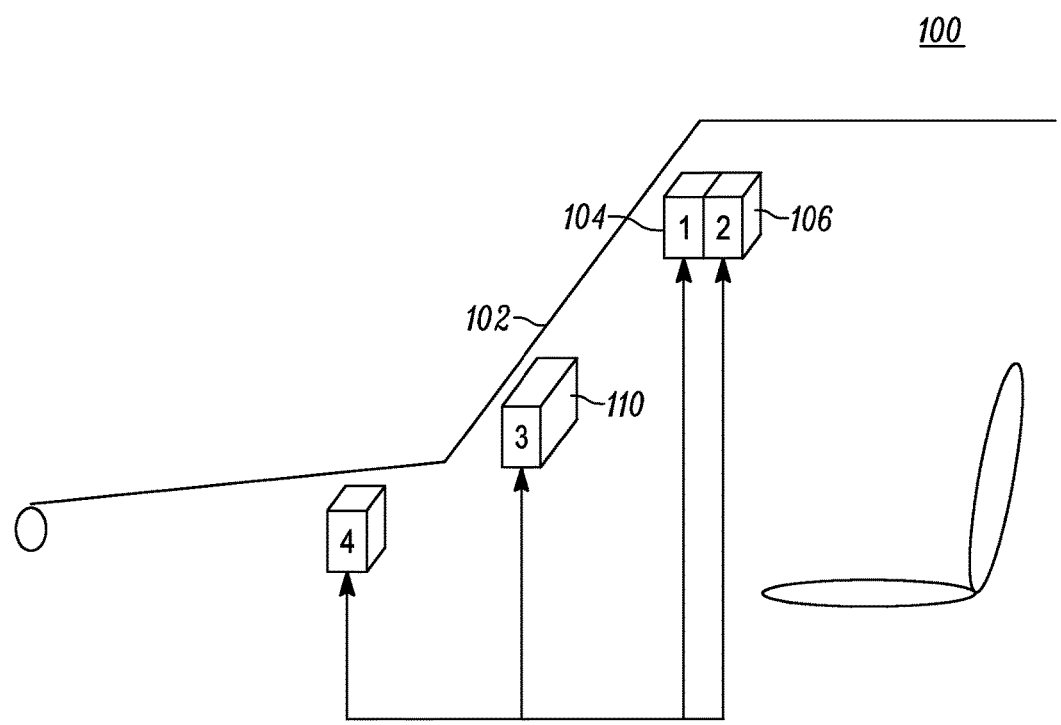
FIG. 1 is a cross sectional view of a vehicle having a road camera configured to provide images of area in front of the vehicle and a driver camera configured to provide images of a driver's eyes.

FIG. 1 depicts a vehicle in cross-section. The vehicle 100 comprises a windshield 102 through which a driver, not shown, can see the road ahead of the vehicle as well as road signs. A first road camera 104 is mounted inside the windshield 102 and configured to be able to "see" area in front of the vehicle, including pavement, right-of-ways, vehicle shoulders and overhead signs. A second camera 106 mounted inside the passenger compartment 108 is directed toward the driver such that the second 106 is able to "see" the drivers head, face and eyes.

Various gauges and instruments are mounted in or form part of a vehicle display panel or dashboard 110, which provide vehicle operating information to a driver. A computer and other electronics 112 is coupled to both cameras 104, 106 and the display 110. The computer and its associated electronics 112 perform various process steps described below.

Figure 2:
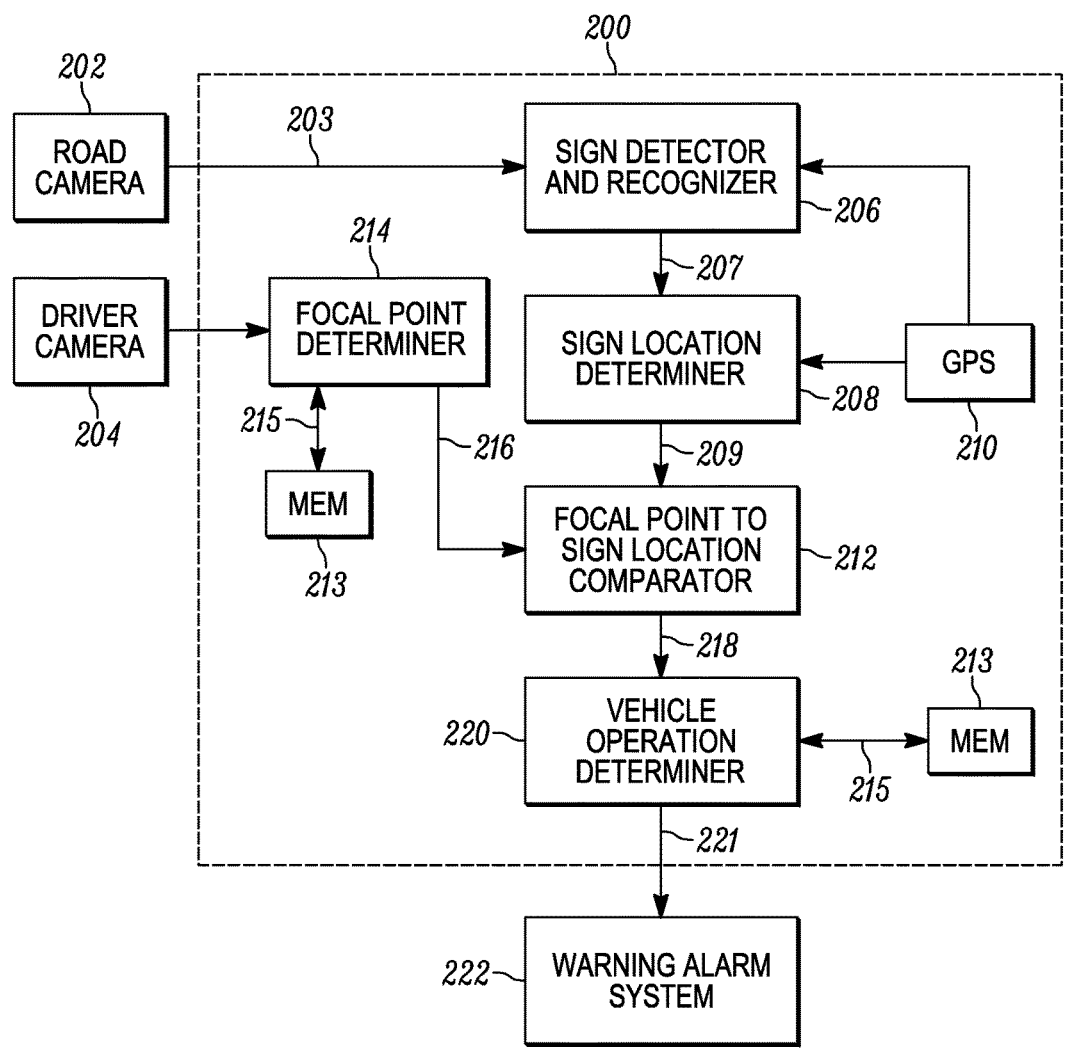
FIG. 2 is a block diagram of a first embodiment of an apparatus for providing advanced traffic sign warnings to a driver of a moving vehicle.

FIG. 2 is a block diagram of an apparatus 200 for providing advanced traffic sign warnings to a driver of a moving vehicle, such as the vehicle 100 depicted in FIG. 1. The apparatus 200 comprises a road camera 202 mounted in a vehicle and which is able to continuously scan areas in front of the vehicle as it moves. The road camera 202 produces data that represents images of the roadway and terrain in front of the vehicle. The images generated by the road camera 202 are frames of individual picture elements or "pixels." Each pixel is represented by digital data 203 that is output from the road camera 202.

A driver camera 204 is mounted in the vehicle at a location where the driver camera 204 is able to send images of a driver's head, face and eyes. As with the road camera 202, the driver camera 204 produces successive images, each individual picture element of which is represented by digital data.

The output 203 of the road camera 202 is provided to a sign detector and recognizer 206, which is an electronic device configured or programmed to recognize various predetermined shapes in images sent to it from the road camera 202. Once a shape in an image is recognized, the content of the recognized sign is also extracted by the sign detector and recognizer. By way of example, in the United States, a stop sign is a hexagon, i.e., it has six equal sides. The "content" of the stop sign is a command to a driver to bring a vehicle to a complete stop at a stop line, usually adjacent to a stop sign. In another example, speed limit signs in the United States are rectangular and usually include the words "SPEED LIMIT" and one or two digits. The "content" of a recognized speed limit sign is the numeric value posted on the sign.

The type or identity of a road sign and its content is provided as digital data 207 to a sign location determiner 208. The sign location determiner 208 is an electronic device configured to determine a physical location of a sign in three-dimensional space. The sign location determiner 208 in combination with the sign detector and recognizer 206 ranks the importance of a recognized road sign by its geographical location relative to the location of the moving vehicle, as determined by a global positioning system 210, its distance from the vehicle, and the content of the sign.

The location of a recognized road sign, its relative importance and location relative to the vehicle are provided as digital data 209 to a focal point and sign location comparator 212. The focal point and sign location determiner is an electronic device that receives information from the driver camera 204 and data from the sign location determiner and determines whether the driver's eyes appear to have fixed on the approaching, recognized road sign.

Referring now to the driver camera 204, images that it produces is sent to the focal point determiner 214. In a preferred embodiment, the focal point determiner 214 is a processor that executes program instructions stored in a non-transitory device 213, which is coupled to the focal point determiner 214 through a conventional address/data/control bus 215.

Using a high-definition (HD) image of the driver's face and eyes, the focal point determiner 214 determines a point in three-dimensional space at which the driver's eyes are focused. Such a determination is made by measuring the distance between the driver's eye pupils, the pupil's angle of inclination and relative angles between the pupils.

The output of the focal point determiner 214 is a digital representation of a point in three dimensional space where the driver's eyes are focused or looking Those of ordinary skill in the art will recognize that the focal point of the driver's eyes will thus change or should change as the driver operates the vehicle. The output 216 of the focal point determiner 214 is provided to the focal point to sign location comparator 212. The comparator continuously monitors the output of the focal point determiner 216 and the output of the sign location determiner 208 to determine if the focal point of the driver's eyes ever equalizes relative to the location of the recognized sign.

The output 218 of the focal point to sign location comparator 212 is provided to a vehicle operation determiner 220. The vehicle operation determiner 220 thus receives a determination of whether the driver appears to have seen a road sign that was recognized and, based upon the identity of the sign as provided by the sign detector and recognizer 206, the vehicle operation determiner 220 determines whether any aspect of the vehicle's operation should be changed based upon the driver seeing or not seeing a particular recognized road sign.

The output 221 of the vehicle operation determiner 220 is provided to an alarm system 222. In a preferred embodiment, the warning alarm system 222 comprises visible displays on a vehicle dashboard or control panel 110 as well as audible alarms output from the vehicles speakers, not shown in FIG. 1 but well known to those of ordinary skill in the art.

Figure 3:
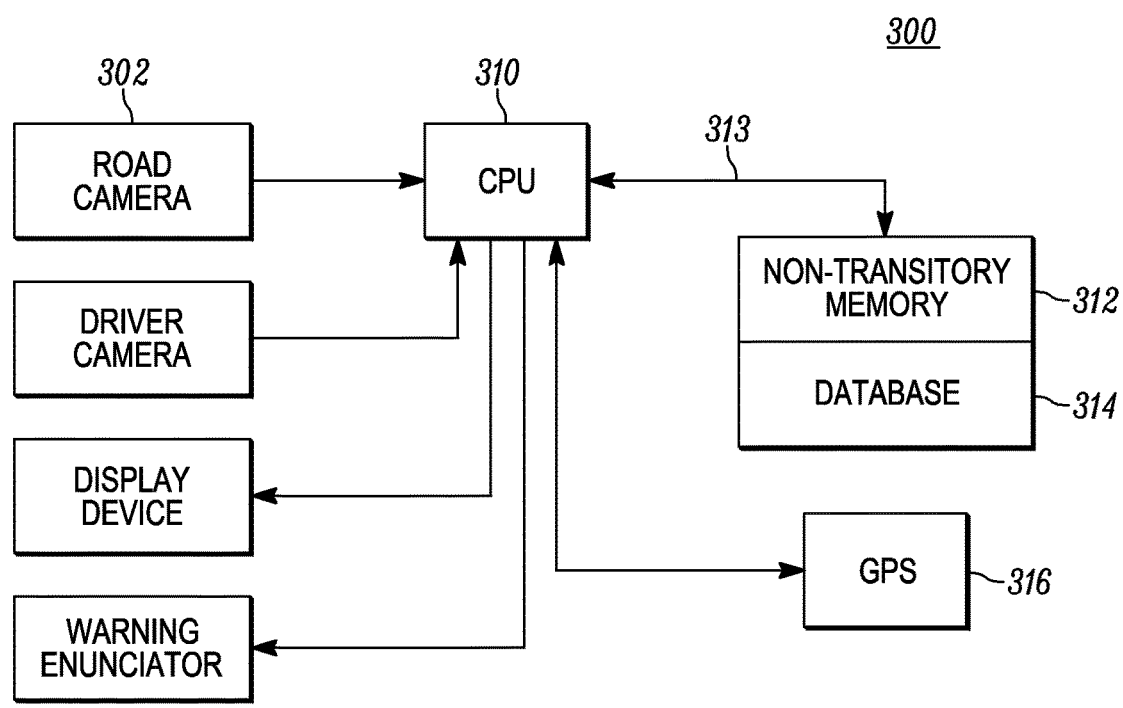
FIG. 3 is a block diagram of a preferred apparatus for providing advanced traffic sign warnings to a driver of a moving vehicle.

FIG. 3 is a block diagram of another apparatus 300 for providing advanced traffic sign warnings to a driver of a moving vehicle but which is implemented by a computer. In FIG. 3, a road camera 302, a driver camera 304, display device 306 and warning enunciator 308 are all coupled to a central processing unit (CPU) or processor 310. The processor 310 is coupled to a non-transitory memory device 312 through a conventional address/data/control but 313.

The non-transitory memory device 312, typically embodied as semiconductor RAM or ROM stores a database 314. The database 314 stores geographic coordinates (location data) for road signs, road speed limit signs and other signs and the information displayed on them.

The database 314 is continuously updated. The locations of recognized signs are provided to the database 314 and stored therein using geographic location information obtained from a GPS navigation system 316 which is also coupled to the processor 310.

Figure 4:
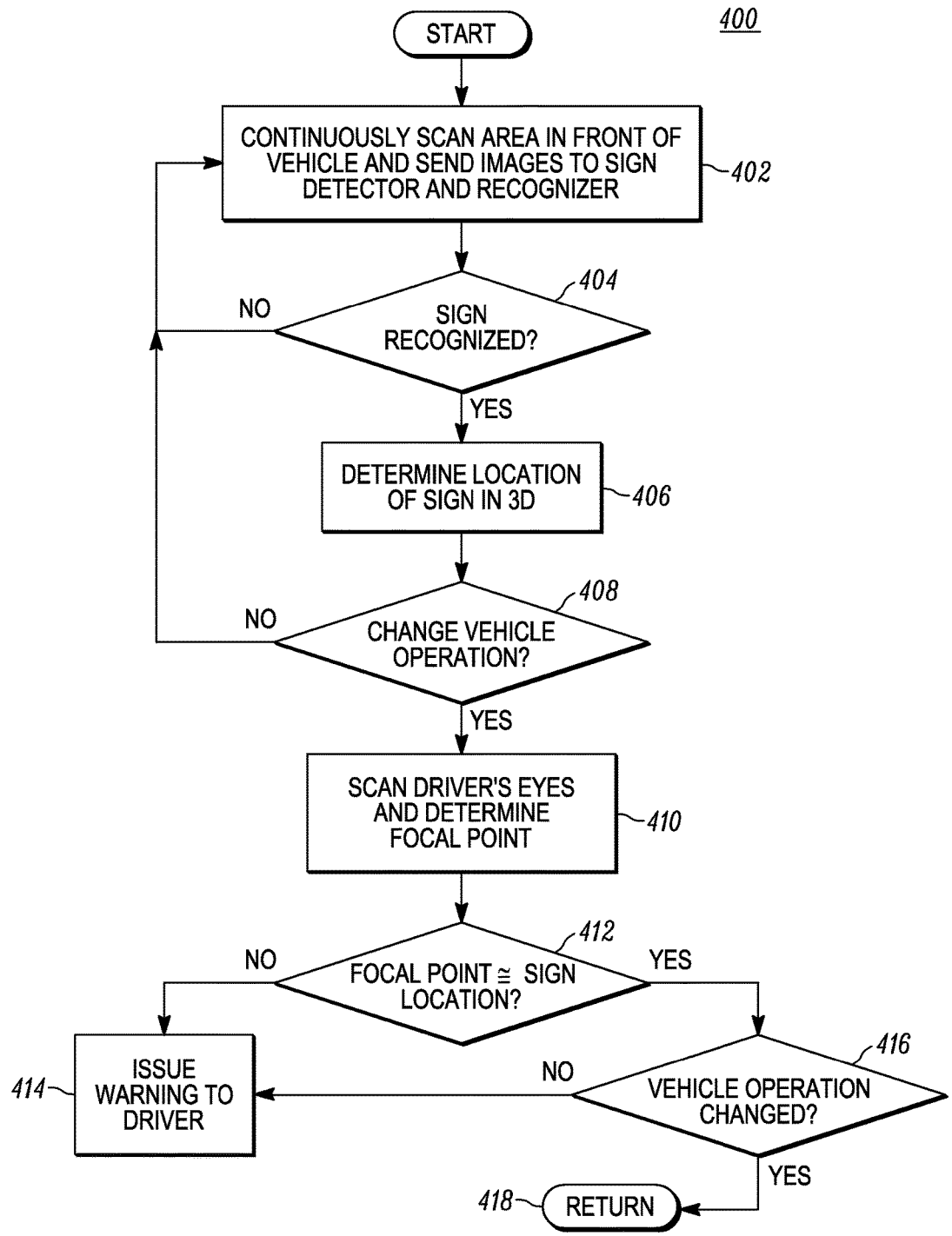
FIG. 4 depicts steps of a method of providing traffic sign warnings to a driver of a moving vehicle.

FIG. 4 depicts steps of a method of providing traffic sign warnings to a driver of a moving vehicle. The method 400 begins at step 402 where the area in front of a vehicle is continuously scanned through step 404 for road signs that are detected and recognized by a road sign detector and recognizer.

When a sign is detected and recognized, the method proceeds to step 406 where the geographic location of the sign relative to the vehicle is determined in three dimensions. The location of the sign relative to the vehicle in three dimensions is accomplished by obtaining the cars geographic location from a global positioning system and shape recognition software executed by a processor.

If the location of a particular recognized sign is such that the vehicle's operation should be changed in some way, a decision is made at step 408 that the vehicle's operation should be changed. Examples of changing a vehicle's operation would be slowing the vehicle down, braking, changing lanes, or completely stopping the vehicle.

At step 410, the driver's eyes are scanned to determine a point in three dimensional space where the driver is presumably looking The scanning and focal point determination performed at step 410 is used at step 412 to determine whether the driver appears to have seen a particular sign the location of which was determined in step 406. If the test at step 412 was negative, which means the driver apparently did not see the sign, a warning is provided to the driver at step 414. Examples of warnings would include visible warning displayed on a dashboard, flashing lights inside or outside the vehicle and an audible warning provided to the driver such as one through the vehicles speakers.

If as a result of the test at step 412 the driver has at least apparently seen a posted road sign, a test is performed at step 416 whether the vehicle's operation has changed or should change. If no vehicle operation has changed after the driver has seen a particular road sign, the method proceeds to step 414 or a warning is issued to the driver again. If the vehicle's operation is being changed appropriately, the method proceeds to step 418 which returns the process to the beginning step 402.

Figure 5:
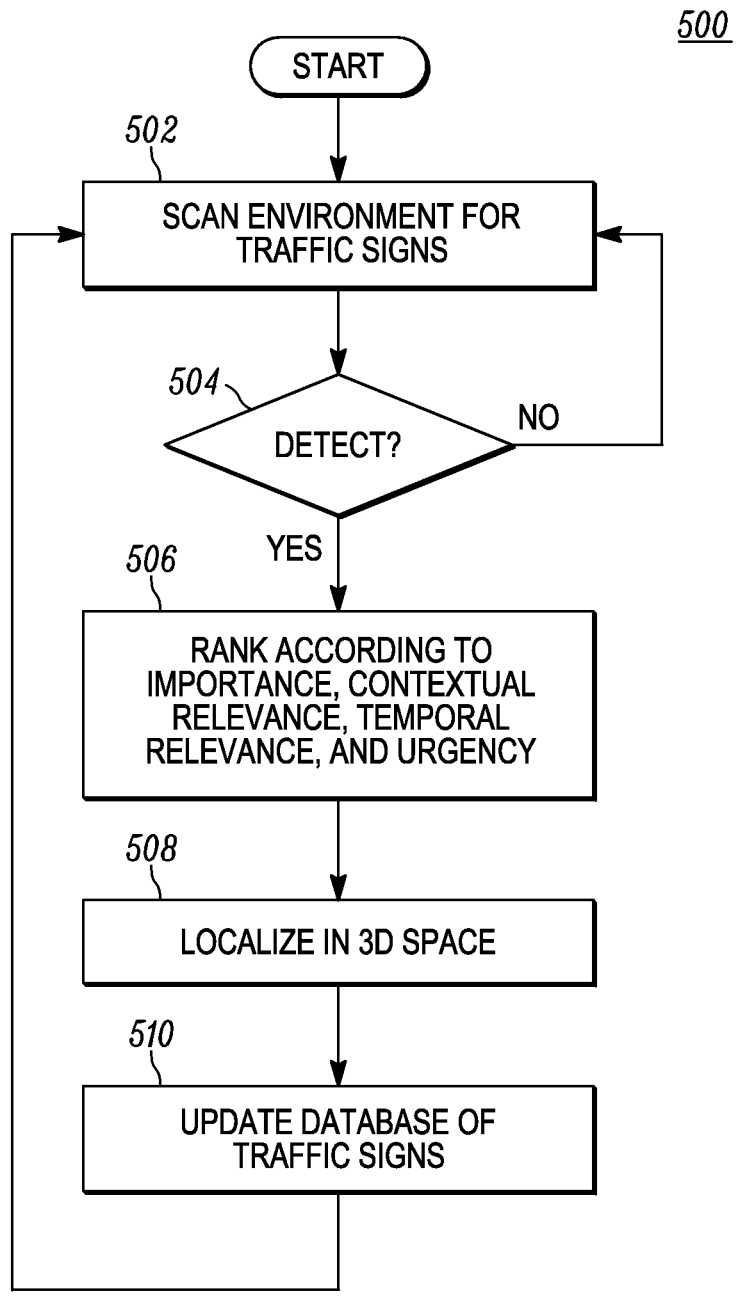
FIG. 5 depicts steps of a method for performing traffic sign recognition and localization.

FIG. 5 depicts steps of a method for performing traffic sign recognition and localization. At step 502, a camera scans a surrounding environment of the vehicle for traffic signs or road signs. Examples of such signs would include a display device such as a lettered board or surface including a stop sign, speed limit sign or a road identification sign. A sign can also be a light or series of lights such as a stop light or flashing warning lights. The method 500 shown in FIG. 5 continuously loops through 502 and 504 until a traffic sign or road sign is detected.

At step 506, a detected road sign is ranked in importance according to its contextual relevance, temporal relevance and urgency. Contextual relevance means that the importance of a sign will depend upon its context. By way of example, a sign identifying the distance to a particular landmark or waypoint will increase in importance as the distance to the landmark or waypoint decreases. Temporal or time relevance will also depend on a distance as well as a time required to reach a location or point on a roadway where a vehicle's operation must change. Urgency determines importance based upon the nature of the recognized sign. By way of example, a stop sign has more urgency than does a speed limit sign or merging sign. A stoplight has more urgency that does a stop sign.

At step 508, the recognized sign is localized in three dimensional space. Localizing a sign in three dimensional space is accomplished using the geographic location of the vehicle and the distance to a particular sign by the size of the recognized sign in an image as well as a location of a sign as determined by a database of road signs.

At step 510, a database of recognized road sign locations is updated.

Figure 6:
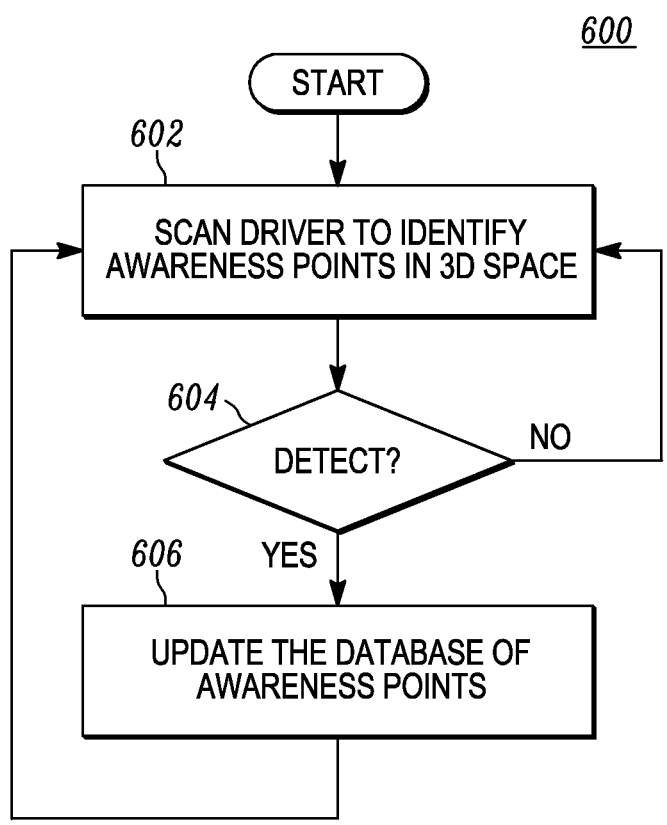
FIG. 6 shows steps of a method for determining whether a driver has seen a particular road sign.

FIG. 6 shows steps of a method for determining whether a driver is aware of or has seen a particular road sign. At step 602, the driver's face, including eyes are scanned by a camera to determine or identify points or locations in 3-D space where the driver appears to be looking or gazing. If a driver's gaze as determined at step 602 is the same or substantially the same as the location of a road sign in 3-D as determined by the method in FIG. 5, the test performed at step 604 results in the method proceeding to step 606 where the database of awareness points is updated.

Figure 7:
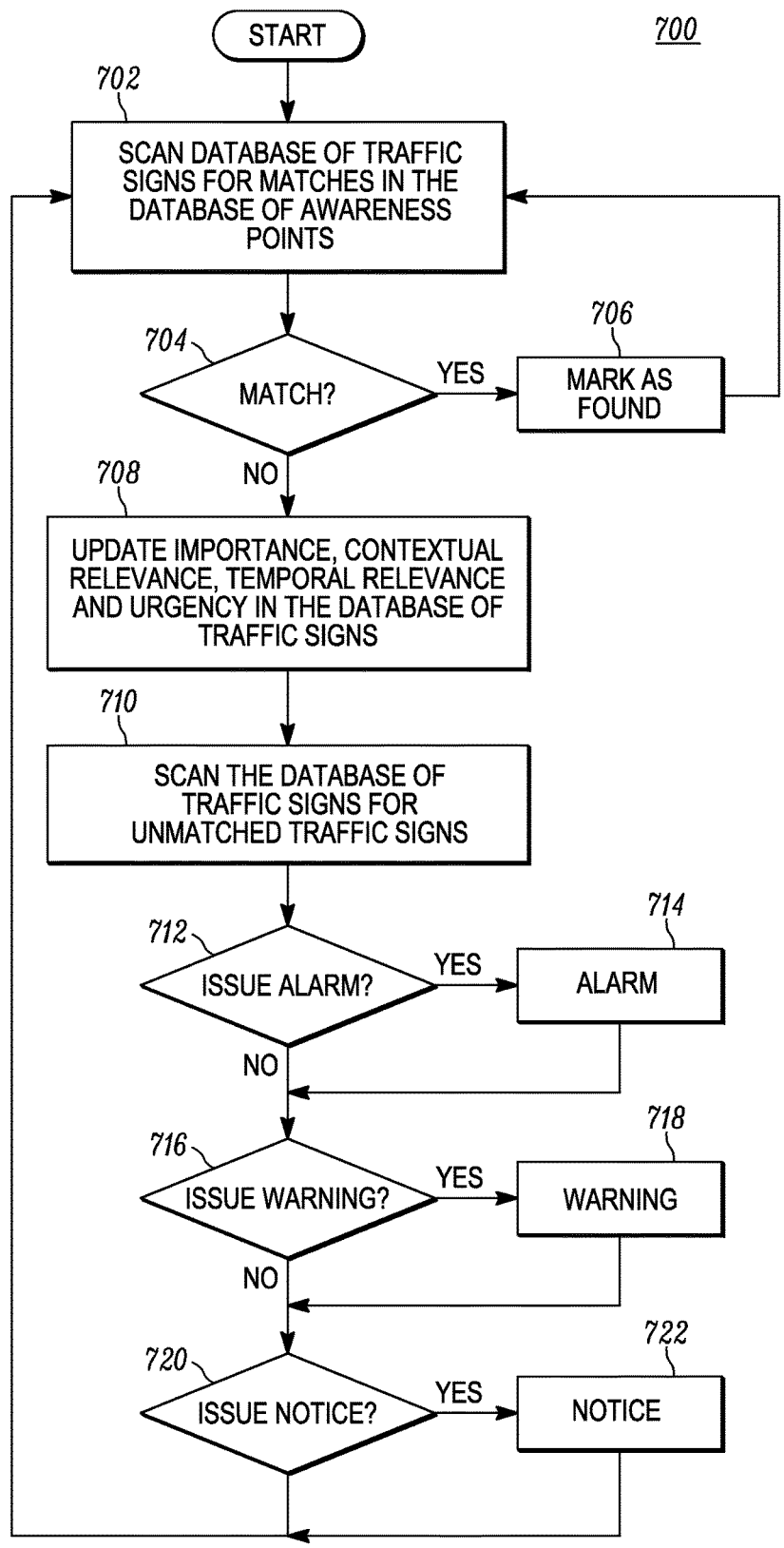
FIG. 7 depicts steps of a method 700 for synchronizing a traffic signs location and driver's awareness to each other.

FIG. 7 depicts steps of a method 700 for synchronizing a traffic signs location and driver's awareness to each other. At step 702, a database of traffic sign locations and traffic sign types is continuously scanned or sorted for matches or occurrences candidates in the database of awareness points, the database of awareness points being created or updated in step 606 as shown in FIG. 6. At step 704, a determination is made whether a match candidate is considered to be a match. If the database of existing and known traffic sign locations matches a geographic location in the database of awareness points, the sign detected in the method shown in FIG. 6 proceeds to step 706 where a recognized sign is added to the database and marked as being "found." If as a result of this test performed at step 704, a determination is made that a recognized sign is not in the database, the method proceeds to step 708 wherein the database of traffic signs is updated to indicate the location, relative importance, contextual relevance and temporal relevance and urgency are updated.

At step 710, the database of traffic signs is scanned and three successive decisions 712, 716, 720 are determined in order to determine the type and nature of the alarm to be provided to the driver.

At step 712, a determination is made whether the urgency and the temporal relevance and contextual relevance are such that an alarm 714 should be issued to the driver. If the sign is not particularly urgent or important, a warning is issued at step 718. Similarly if the nature and relevance and importance of the sign do not warrant a warning, a simple notice is issued at step 722.

The foregoing description is for purposes of illustration only. The true scope of the invention is set forth in the following claims.

What is claimed is:

1. A method of providing traffic sign warnings to a driver of a moving vehicle, the method comprising:
   optically scanning an area in front of the moving vehicle to obtain an image of said area in front of the moving vehicle;
   detecting and recognizing a road sign in said image;
   determining a location of the recognized road sign relative to the moving vehicle by localizing the recognized road sign in three-dimensions using geographic coordinates associated with the moving vehicle and a distance between the moving vehicle and the recognized road sign obtained from the image;
   determining a first vehicle operation parameter that should be changed responsive to the recognized road sign;
   optically scanning the driver's head and eyes;
   calculating at least one focal point of the driver's eyes from said optically scanning the driver's head and eyes;
   determining whether the driver has seen the recognized road sign from the calculated at least one focal point of the driver's eyes and the determined location of the recognized road sign relative to the moving vehicle;
   determining whether the driver has changed a vehicle operation parameter;
   if the driver has not changed the vehicle operation parameter, providing a first warning to the driver responsive to the recognized road sign; and
   updating a database of road sign locations with the determined location of the recognized road sign.

2. The method of claim 1, wherein determining whether the driver has seen the recognized road sign comprises:
   comparing the calculated focal point of the driver's eyes to the determined location of the recognized road sign; and
   determining the recognized road sign to have been recognized if:
      the calculated focal point of the driver's eyes and the determined location of the recognized road sign are substantially the same; and
      the driver has changed or is changing the vehicle operation parameter that is consistent with the recognized road sign.

3. The method of claim 1, wherein determining the first vehicle operation parameter that should be changed responsive to the recognized road sign comprises:
   ranking the recognized road sign according to at least one of:
      importance; contextual relevance; temporal relevance; and urgency.

4. The method of claim 1, wherein providing the first warning comprises providing a visible indicator on a vehicle control panel.

5. The method of claim 1, wherein providing the first warning comprises providing an audible alarm inside a passenger compartment of the moving vehicle.

6. The method of claim 1, further comprising automatically changing the first vehicle operation parameter after providing the first warning to the driver.

7. The method of claim 6, wherein automatically changing the first vehicle operation parameter comprises automatically applying vehicle brakes.

8. An apparatus for providing traffic sign warnings to a driver of a vehicle when the vehicle is moving, the apparatus comprising:
   a first camera configured to scan an area in front of the vehicle to obtain an image;
   a road sign detector and recognizer coupled to the first camera, the road sign detector and recognizer configured to detect and recognize a road sign in said image;
   a road sign location determiner configured to determine a location of the recognized road sign relative to the vehicle by localizing the recognized road sign in three-dimensions using geographic coordinates associated with the vehicle and a distance between the vehicle and the recognized road sign obtained from the image;
   a vehicle operation parameter controller configured to determine a first vehicle operation parameter that should be changed responsive to the recognized road sign;
   a second camera directed at the driver and configured to optically scan the driver's head and eyes and obtain at least one image of the driver's eyes;
      a driver's eye focal point determiner configured to calculate at least one focal point of the driver's eyes from said at least one image of the driver's eyes;
   a recognized road sign determiner, configured to determine whether the driver has seen the recognized road sign from the calculated at least one focal point of the driver's eyes and the determined location of the recognized road sign;
   an operation parameter determiner configured to determine whether the driver is changing the first vehicle operation parameter;
   a controller configured to provide a first warning to the driver if the driver does not change the first vehicle operation parameter responsive to the recognized road sign; and
   a database configured to be updated with the determined location of the recognized road sign.

9. The apparatus of claim 8, wherein the road sign detector and recognizer, the road sign location determiner and the vehicle operation parameter controller comprise a computer, operatively coupled to a non-transitory memory device storing program instructions for the computer.

10. The apparatus of claim 8, wherein the driver's eye focal point determiner, the recognized road sign determiner and the operation parameter determiner comprise a computer, operatively coupled to a non-transitory memory device storing program instructions for the computer.

11. The apparatus of claim 8, further comprising a display device configured to display a message to the driver responsive to the controller providing the first warning.

12. The apparatus of claim 8, further comprising an audio device configured to provide a predetermined sound inside the vehicle responsive to the controller providing the first warning.

* * * * *